US00PP37568P2

(12) United States Plant Patent
Byrne et al.

(10) Patent No.: US PP37,568 P2
(45) Date of Patent: Aug. 11, 2026

(54) PEACH TREE NAMED 'TRH3C113LW'

(50) Latin Name: *Prunus persica*
Varietal Denomination: TRH3C113LW

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,365

(22) Filed: Sep. 22, 2025

(51) Int. Cl.
*A01H 5/08* (2018.01)

(52) U.S. Cl.
USPC ..... Plt./195

(58) Field of Classification Search
USPC ..... Plt./156, 180, 194, 195
See application file for complete search history.

(56) References Cited

U.S. PATENT DOCUMENTS

PP26,119 P3 11/2015 Byrne et al.
PP28,077 P3 6/2017 Byrne et al.

OTHER PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,375, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.
Rawandoozi, May 2019, QTL Mapping Through Pedigree-Based Analysis for Six Phenological and Quality Traits in Peach. Dissertation for Doctor of Philosophy. Texas A&M University.

*Primary Examiner* — Karen M Redden
(74) *Attorney, Agent, or Firm* — Dentons US LLP

(57) ABSTRACT

Disclosed is a new variety of *Prunus persica* named 'TRH3C113LW'. This new variety, which requires approximately 300 chilling units of dormancy, is a peach tree of early mid-season maturity, which produces white-fleshed, subacid fruit that are firm with a 60-80% red blush over a light-yellow ground color, and suitable for the fresh fruit market.

5 Drawing Sheets

Latin name of the genus and species of the plant claimed: *Prunus persica.*

Variety denomination: 'TRH3C113LW'.

CROSS-REFERENCE TO RELATED APPLICATIONS

Peach trees developed under the same breeding program as 'TRH2E120LW' include the co-pending applications listed below.

| U.S. application Ser. No. | Title |
|---|---|
| U.S. 19/336,141 | PEACH TREE NAMED 'TX3C490LWP' |
| U.S. 19/336,148 | PEACH TREE NAMED 'TRH2E68L' |
| U.S. 19/336,164 | PEACH TREE NAMED 'TRH3B53L' |
| U.S. 19/336,169 | PEACH TREE NAMED 'TRH3C114W' |
| U.S. 19/336,358 | PEACH TREE NAMED 'TRH2E121L' |
| U.S. 19/336,361 | PEACH TREE NAMED 'TRH3A17' |
| U.S. 19/336,363 | PEACH TREE NAMED 'TRH2E120LW' |
| U.S. 19/336,368 | PEACH TREE NAMED 'TRH3E88LW' |
| U.S. 19/336,370 | PEACH TREE NAMED 'TX2B449LW' |
| U.S. 19/336,372 | PEACH TREE NAMED 'TX2C465CW' |
| U.S. 19/336,375 | PEACH TREE NAMED 'TX2C465CW' |
| U.S. 19/336,377 | PEACH TREE NAMED 'TRH3C111' |
| U.S. 19/336,380 | PEACH TREE NAMED 'TRH2C108W' |

-continued

| U.S. application Ser. No. | Title |
|---|---|
| U.S. 19/336,383 | PEACH TREE NAMED 'TRH2E116L' |
| U.S. 19/336,385 | PEACH TREE NAMED 'TRH2B102LW' |

BACKGROUND OF THE INVENTION

This invention relates to peach trees and, more specifically, to peach trees referred to as a variety of *Prunus persica* named 'TRH3C113LW', which requires approximately 300 chilling units of dormancy, produces a firm, clingstone, white-fleshed, subacid peach with a 60-80% red blush over a light-yellow ground color that matures early mid-season. The present peach tree was the result of an ongoing Stone Fruit Breeding Program in College Station, Brazos County, Texas. To this end, controlled crosses were made each year to produce seedling populations from which improved progenies are evaluated and selected. The seedling 'TRH3C113LW' was derived from a population of seedlings derived by crossing the white-fleshed, subacid, nectarine 'Smooth Delight One' (patented, U.S. Plant Pat. No. 28,077) with the low-chill, acid-sweet, yellow-fleshed peach 'Tex- First' (patented, U.S. Plant Pat. No. 26,119P3). The seed from the hybrid population from the 'Smooth Delight One' x 'TexFirst' cross were embryo rescued and seedlings planted in 2011 in an experimental plot in Floresville, TX. 'TRH3C113LW' was marked for subsequent observation in 2013 and noted as having exceptional characteristics.

'TRH3C113LW' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year and older trees in Pleasanton (2018-2019, 2023), Fairfield (2015-2018) and Somerville (2017-2023) Texas. This evaluation clearly demonstrated that the re-propagated trees were true to the characteristics of the original seedling in all observable aspects.

SUMMARY OF THE INVENTION

The 'TRH3C113LW' peach is characterized by requiring 300 chill units to fruit and producing clingstone, white-fleshed, subacid fruit that ripens in the early mid-season and produces a firm fruit with a 60-80% red blush over a light-yellow ground color. In this regard, the present variety of peach tree bears fruit that are ripe for commercial harvesting and shipment in late May to early June, when the fruit is grown in the medium chill zone of Texas. 'TRH3C113LW' blooms 3 days before and ripens 3-4 weeks after its female parent 'Smooth Delight One' (patented, U.S. Plant Pat. No. 28,077) and blooms 2 weeks after and ripens 5 weeks after its pollen parent 'TexFirst' (patented, U.S. Plant Pat. No. 26,119). 'TRH3C113LW' differs from its subacid, white fleshed nectarine female parent, 'Smooth Delight One', as it is a peach and from its yellow-fleshed, acid-sweet, low chill peach pollen parent, 'TexFirst', as it has subacid, white flesh and requires ~150 chill hours more to fruit.

'TRH3C113LW', a subacid, white-fleshed peach differs from two commercial subacid, white-fleshed cultivars, 'White Delight One' (not patented, US App. Pub. No. 2016/0205833 P1, abandoned) and 'White Delight Two' (not patented, US App. Pub. No. 2016/0205832 P1, abandoned) as it has reniform versus globose glands, showy versus non showy flowers, requires 250 less chilling hours to fruit properly, and blooms 2 to 2½ weeks before these two commercial cultivars. In addition, 'TRH3C113LW' ripens about 3½ weeks later than 'White Delight One' and about 4 days before 'White Delight Two'. This new subacid, white-fleshed peach exhibits potential to be commercialized in regions that have chilling requirements that are low.

BRIEF DESCRIPTION OF THE DRAWINGS

This new variety of peach tree is illustrated by the accompanying photographs of 3-year old to 5-year old plants grown in Somerville and Pleasanton, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
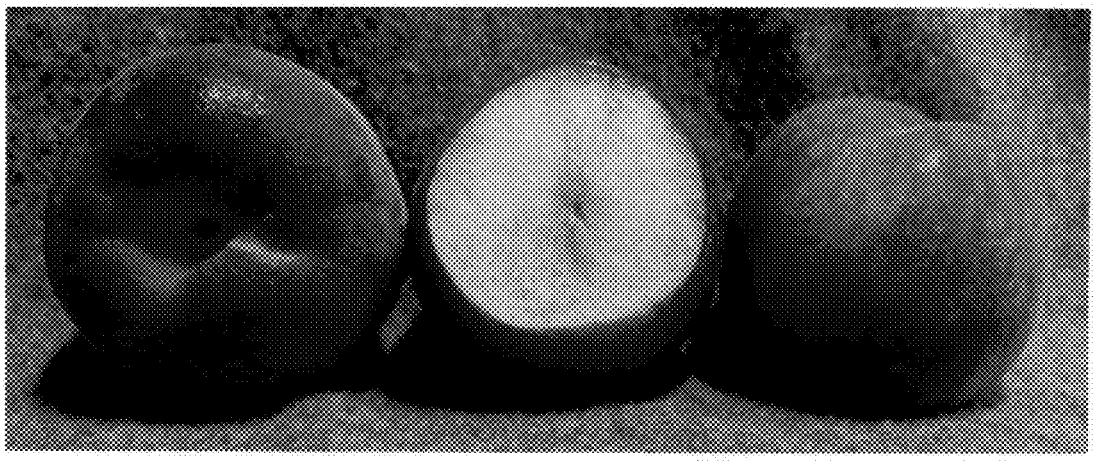
FIG. 1. Fruit of 'TRH3C113LW' produced in Somerville, Texas showing external and internal coloration.
Figure 2:
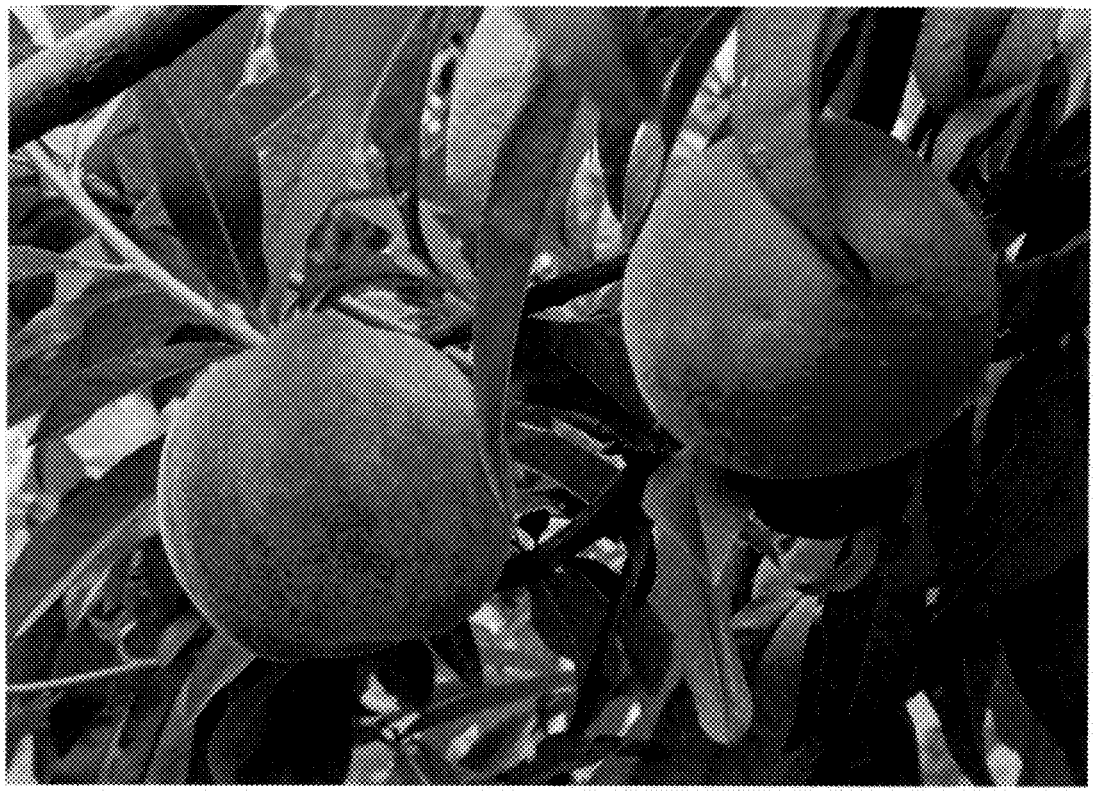
FIG. 2. 'TRH3C113LW' fruit produced in Pleasanton, Texas showing shape and external coloration.
Figure 3:
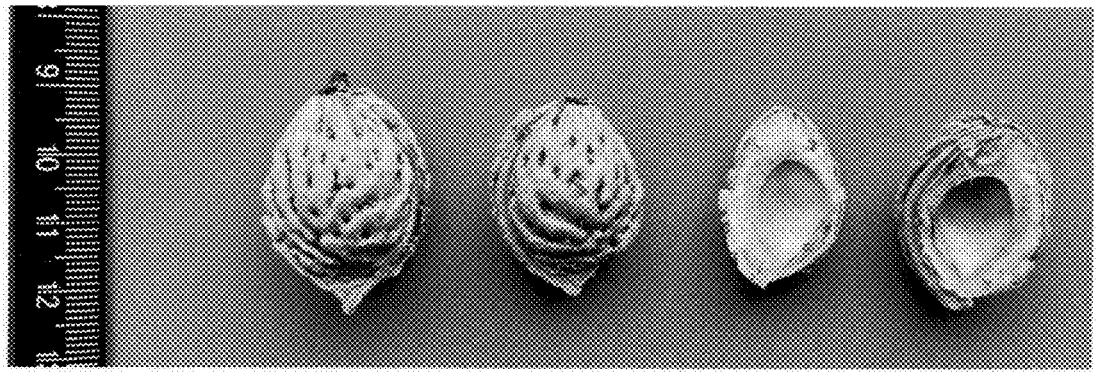
FIG. 3. Photograph of the endocarps of 'TRH3C113LW' peach. The ruler is in centimeters.
Figure 4:
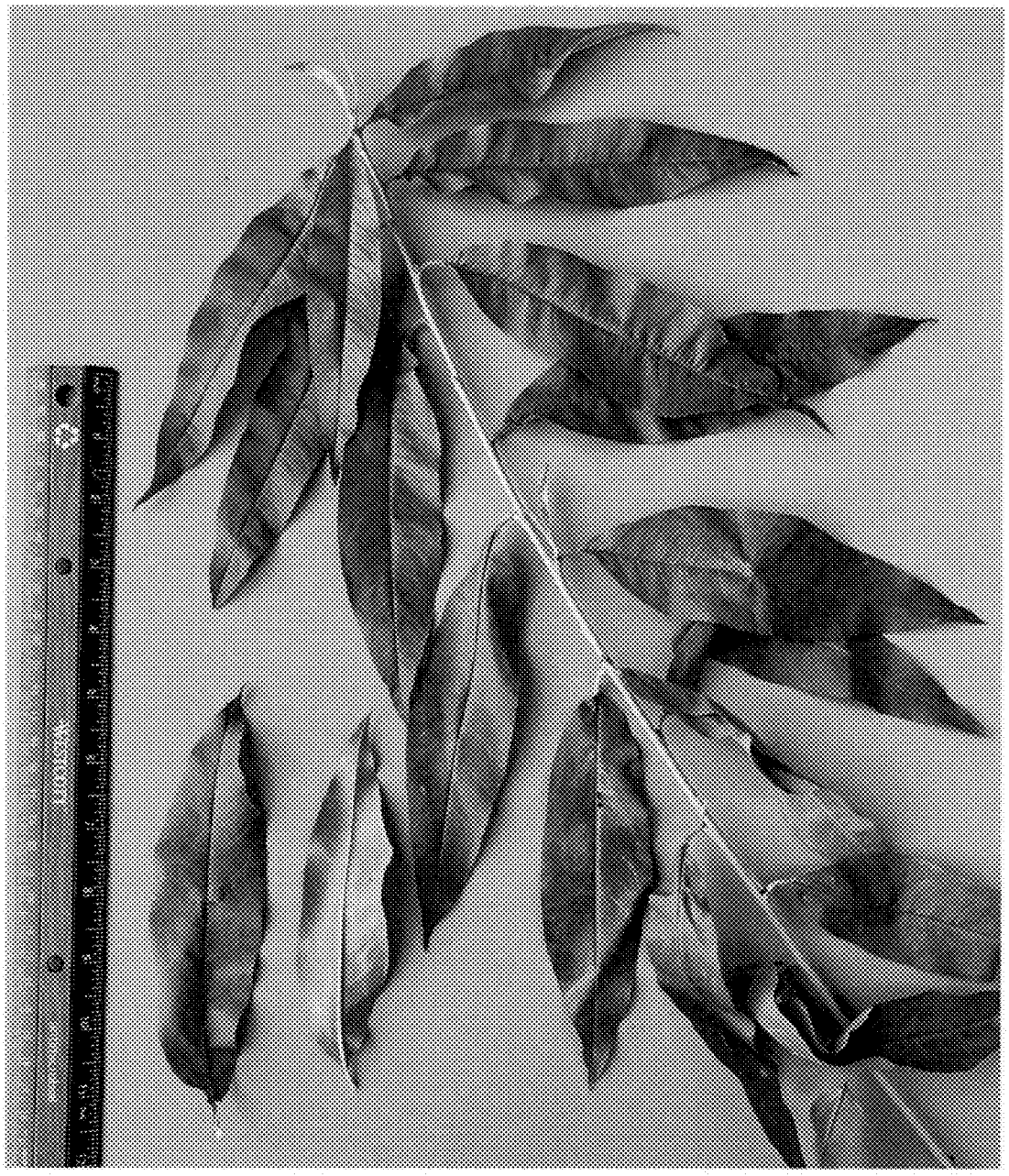
FIG. 4. A stem showing the leaves of 'TRH3C113LW' peach. The ruler is in centimeters.
Figure 5:
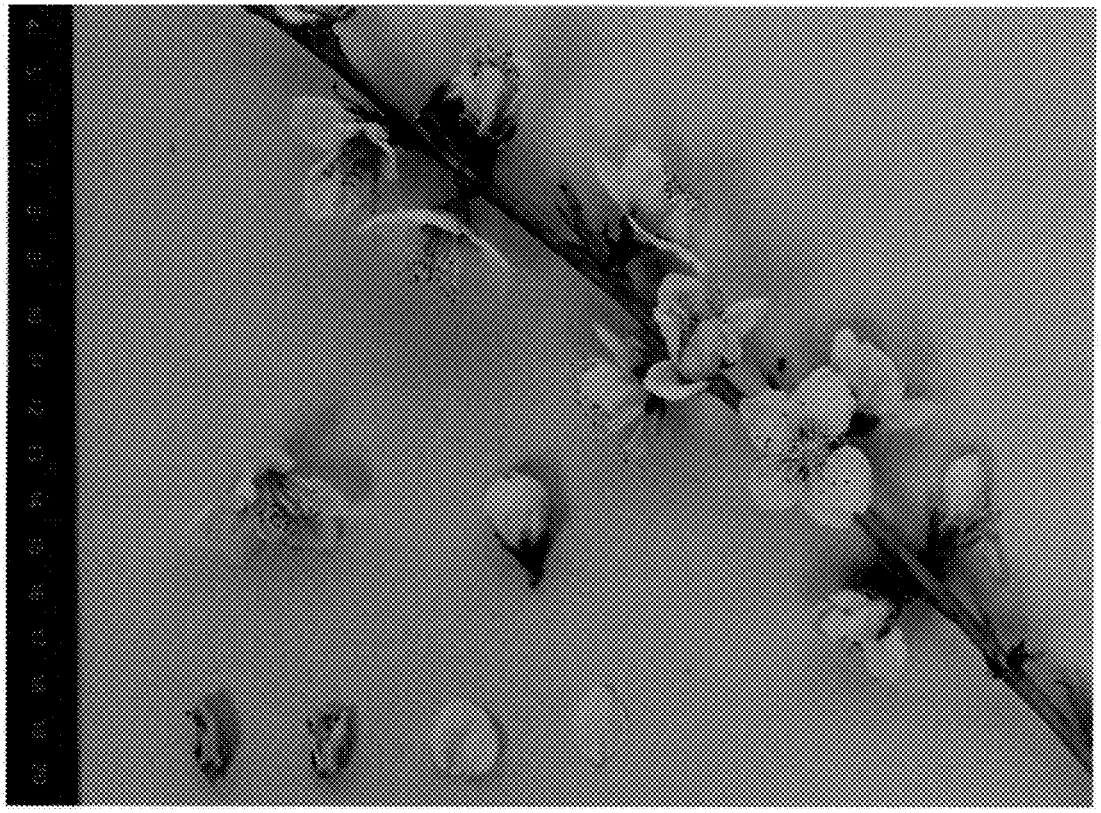
FIG. 5. A stem showing the flowers of 'TRH3C113LW' peach. The ruler is in centimeters.

Referring more specifically to the pomological details of this new and distinct variety of peach tree, the following has been observed under the ecological conditions prevailing at the experimental orchards in the medium chill zone of Texas (Fairfield and Somerville). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average as compared to other common peach cultivars ripening in the medium chill zone of Texas.

*Height*.—7.5 feet (2.3 m) at the end of the 2024 growing season.

*Width*.—7 feet width (2.1 m) at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape*.—The 'TRH3C113LW' peach has been trained to an open center configuration but exhibits a semi spreading growth type as seen in peach varieties 'Texprince' (U.S. Plant Pat. No. 14,629) and 'Texking' (U.S. Plant Pat. No. 14,627).

*Current season growth*.—The current season growth for the new variety was approximately 1 to 3 feet (0.3-0.9 m). Vigor is medium compared to other common peach varieties grown in the medium chill zone of Texas.

*Regularity of bearing*.—Regular in the absence of temperatures of 28° F. or below during bloom and considered hardy in the medium chill zone of Texas.

Trunk:

*Size*.—Approximately 2.5 inches (6.35 cm) in diameter and 8.75 inches (22.2 cm) in circumference when measured at a distance of approximately 12 inches (30.5 cm) above the soil level, at the end of the 2024 growing season on a three-year old tree.

*Bark texture*.—Considered moderately rough with numerous folds of papery scarf-like skin being present.

*Bark coloration*.—Variable, colors (RHS2001) present are 156D of the Greyed-White Group, 164A, 165A, 165B, 166A, 167A and 176A of the Greyed-Orange Group, 198D of the Greyed-Green Group, N200D of the Brown Group and 201D of the Grey Group.

Branches:

*Thickness*.—Average. Approximately 3.5 cm in diameter as measured 10 cm from the trunk on a five-year old tree) as compared to other varieties.

*Surface texture*.—Average and appearing furrowed on wood that is several years old.

*Lenticels*.—Numerous flat, oval lenticels present. The lenticels range in size from approximately 4 to 7 mm in width and were approximately 1 to 2 mm in height.

*Current season shoots*.—Surface texture — Substantially glabrous.

*Internode length*.—Approximately 15 to 16 mm as measured in the middle of a current season stem.

*Color of mature branches*.—The predominant colors (RHS2001) are 156D of the Greyed-White Group, 164A, 165B, 166B and 177B of the Greyed-Orange Group and 200D and N200D of the Brown Group.

*Current season shoots*.—Color (RHS2001) — Medium to light green, 155B, 155C, 155D, N144C, N144D and 145A of the Yellow-Green Group and with some reddish-brown coloration appearing on exposed surface of the shoots 165A, 166A, 166B, 175A and 176A of the Greyed-Orange Group.

Leaves:

*Size*.—Considered moderately large for the species. Leaf measurements have been taken from vigorous upright current season growth approximately at mid-shoot.

*Leaf length*.—Approximately 157 to 171 mm.

*Leaf width*.—Approximately 41 to 49 mm.

*Leaf thickness*.—Less than 1 mm.

*Leaf form*.—Lanceolate.

*Leaf tip form*.—Acuminate.

*Leaf upper surface color* (*RHS*2001).—Green, approximately 137A, 137B and 137C of the Green Group.

*Leaf lower surface color* (*RHS*2001).—Green, approximately 137C and 137D of the Green Group.

*Leaf lower mid-vein color* (*RHS*2001).—Light yellow green, 145C, 145D and 150D of the Yellow-Green Group.

*Leaf margins*.—Form — Considered crenate. Uniformity — Considered generally uniform.

*Leaf petioles*.—Length — Approximately 12 to 13 mm. Thickness — Approximately 2 mm. Texture — Glabrous. Color (RHS2001) — Pale green, 145C, 145D and 150D of the Yellow-Green Group.

Leaf glands.—Size — Approximately 1.5 to 2 mm in height and 1 mm in width. Number — Generally 1 to 2 per leaf. Type — Reniform. Color (RHS2001) — Green, 144B, N144D, 145A, 145C and 146D of the Yellow-Green Group.

*Leaf stipules*.—Length — Approximately 12 to 16 mm. Form — Lanceolate. Color (RHS2001) — Green, 144A and N144D of the Yellow-Green Group. The stipules are considered to be early deciduous. Ratio of flower to vegetative buds — Generally 2 flower buds per vegetative bud.

Flowers:

*Floral buds*.—General — The floral buds are considered to be conic in form, and slightly appressed relative to the bearing shoot. Color (RHS2001) — Mature buds are brown, (approximately 164A, 165A, 166A and 166B of the Greyed-Orange Group and 200C of the Brown Group). Mature Bud Length — 5-6 mm. Mature Bud Width — 3-4 mm.

*Blooming type*.—Mean date of full bloom in the medium chill zone of Texas was in mid-February (February 12$^{th}$ at Somerville and Fairfield experimental plots), 3 to 10 days before the commercial cultivars 'Texking' (patented, U.S. Plant Pat. No. 14,627) and 'Flordaking' (not patented).

*Flower type*.—Showy.

*Flower size*.—Flower diameter at full bloom is approximately 39 to 41 mm.

*Bloom quantity*.—Considered abundant.

*Flower bud frequency*.—Normally 1 to 2 per node.

*Petal size*.—General — Considered medium to medium large for the species. Width — Approximately 11 to 13 mm. Length — Approximately 17 to 19 mm.

*Petal form*.—Broadly ovate.

*Petal number*.—Nearly always 5 per flower.

*Petal color* (*RHS*2001).—Light to medium pink when young (62D, 69A and 73D of the Red-Purple Group and 75C and 75D of the Purple), becoming darker with advancing senescence.

*Petal claw*.—Form-The claw is considered truncate in shape. Length — Approximately 2 mm. Width — Approximately 1 mm.

*Petal margins*.—Generally considered variable, from nearly smooth to slightly undulate.

*Petal apex*.—Generally-The petal apices appear rounded.

*Flower pedicel*.—Length-Average length of approximately 2 mm. Thickness-Approximately 1 to 1.5 mm. Color (RHS2001)-A light green (145A and 145B of the Yellow-Green Group).

*Floral nectaries*.—Color (RHS2001) — Medium yellow-orange (13B, 13C and 14C of the Yellow Group and 15A, 15C and 16B of the Yellow-Orange).

*Sepals*.—Sepal number — Generally five per flower. Surface Texture — The surface has a short, fine, woolly texture. Size — Height 5.3 mm, Width 4.6 mm. Form — Ovate. Color (RHS2001) — Maroon and green with white (approximately 60B of the Red-Purple Group; 144C, 144D, 145A, 145B and 145C of the Yellow-Green Group and 155A, 155B, 155C, and 155D of the White Group).

*Floral cup* (*hypanthium*).—Surface Texture — Generally glabrous. Color (RHS2001) — Maroon with green (approximately 60B of the Red-Purple Group and 144C, 144D, 145A, 145B and 145C of the Yellow-Green Group).

*Anthers*.—Color (RHS2001) — Medium yellow with red-orange (approximately 4B, 4C, 5C, 5D, 8B, 8C, 8D, 9C, 9D, 10A, 10B and 10C of the Yellow Group and N25A and N25B of the Orange Group).

*Pollen production*.—Pollen is abundant and is a light to medium yellow color (approximately RHS2001 2B, 2C, 3C, 3D, 4B, 4C and 5D of the Yellow Group).

*Filaments*.—Size — Variable in length, approximately 13 to 17 mm, with the filaments approximately equal to height of the pistil and below the height of the petals. Color (RHS2001) — White (approximately 155A, 155B, 155C and 155D of the White Group) and darkening with advanced maturity.

*Pistil*.—General — Approximately equal to the height of the anther and below the height of the petals.

Length — Approximately 12 to 17 mm, including the ovary. Color (RHS2001) — Considered white when young (approximately 155A, 155B, 155C and 155D of the White Group) and becoming darker with advancing senescence.

*Surface texture*.—The variety has a long, silver white pubescent pistil (approximately RHS2001 155A, 155B, 155C and 155D of the White Group).

Fruit:

*Maturity when described*.—The present variety of fruit is described, as it would be found in its firm ripe condition at full commercial maturity. Under the ecological conditions prevailing in the medium chill zone of Texas it would be ripe in late May to Early June. The average ripe date at Pleasanton, Somerville, and Fairfield experimental plots was May 20$^{th}$, June 2$^{nd}$, and May 30$^{th}$ respectively.

*Size*.—General — Medium large to large for the season and considered uniform. Average Cheek Diameter — Approximately 65 to 68 mm. Average Suture Diameter — Approximately 63 to 67 mm. Average Axial Diameter — Approximately 57 to 64 mm.

*Fruit form*.—Generally considered round. Rarely, the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — Maroon. Approximately 53A of the Red Group, 59A, 59B and 60A of the Red-Purple Group and 183A, 183B, 183C, 184A, 184B, 185A, 187A, 187B and 187C of the Greyed-Purple Group.

*Ventral surface*.—Form-Considered uniform.

*Stem cavity*.—Width — Approximately 16 to 21 mm. Length — Approximately 21 to 26 mm. Depth — Approximately 9 to 11 mm.

*Fruit base*.—Flat.

*Fruit apex*.—Flat.

*Fruit stem*.—Length — 7 to 8 mm. Thickness — 3 to 4 mm. Color (RHS2001) — Light yellow green. 144D and N144A of the Yellow-Green Group.

*Fruit skin*.—Generally considered medium or average in thickness. Surface Texture — Light, short pubescence. Skin Acidity — Considered neutral. Tenacious to Flesh — Yes at commercial maturity. Tendency to Crack — Cracking not observed. Skin Color — Generally-Variable, with approximately 60-80% of the fruit surface covered with a medium to dark red blush. The fruit skin over color pattern varies from marbled to solid. Blush Color (RHS2001) — Medium to dark red. 39A, 46A, 47A, 47B, 47C, 48A and 53A of the Red Group, 59A, 59B and 60A of the Red-Purple Group and 183A, 183B, 183C, 186C, 187C and 187D of the Greyed-Purple Group. Skin Ground Color (RHS2001)-Light yellow. Approximately 4D, 5D, 8C, 8D, 9C, 11C and 11D of the Yellow Group.

*Flesh color* (*RHS*2001).—White with red flecks. Approximately 4D, 8D and 11D of the Yellow Group, 46A, 47A and 47B of the Red Group, 155B and 155D of the White Group and 158D of the Yellow-White Group. Anthocyanin intensity in the flesh is generally weak to medium next to the skin, centrally and next to the stone.

*Flesh fibers*.—Present throughout the flesh.

*Stone cavity color* (*RHS*2001).—Light yellowish green. Approximately 1A, 1B, 1C and 1D of the Green-Yellow Group, 2C, 3C, 3D and 4C of the Yellow Group and 150D of the Yellow-Green Group.

*Flesh texture*.—Generally, the flesh is considered firm at commercial maturity.

*Ripening*.—Generally the fruit of the present variety ripens evenly.

*Flavor*.—Considered very sweet (Average Brix 13.2) with rich subacid flavor.

Stone:

*Attachment*.—Clingstone to semifreestone at commercial maturity.

*Stone size*.—Generally considered medium to medium-large relative to the ratio of stone to fruit size. Length — Approximately 29 to 31 mm. Width — Approximately 22 to 23 mm. Thickness — Approximately 16 to 18 mm.

*Fibers*.—Generally a few fibers are attached along the entire surface of the stone.

*Stone form*.—Variable. Elliptical to ovate.

*Stone base*.—The stone base is medium to wide.

*Base angle*.—Considered medium to wide.

*Hilum*.—Generally considered rather poorly defined as is common in early ripening varieties. The hilum is approximately 3 to 5 mm long and less than 1 mm wide.

*Stone apex angle*.—Wide.

*Stone shape*.—Considered elongated.

*Stone surface*.—Surface Texture — Contains single pits, rosettes and chains of pits. Ridges — Numerous fine ridges are present basally and converge towards the base of the stone.

*Ventral edge*.—Medium.

*Dorsal edge*.—Shape — Grooved and having moderately rough edges.

*Stone color* (*RHS*2001).—The color of the dry stone is medium to light brown, 164B, 164C, 165C and 165D of the Greyed-Orange Group. The color of the inside surface of the endocarp is primarily medium to light brown, 158A of the Yellow-White Group and 164C, 164D and 165D of the Greyed-Orange Group.

*Tendency to split*.—Splitting not observed.

*Kernel*.—The kernel fills the endocarp at harvest and measures approximately 5-7 mm in thickness, 10-12 mm in width, and 15-16 mm in length. Colors (RHS2001) of the fresh kernel are varying shades of light yellow, 4D, 5D, 8D, 9D, 10D,11C, 11D, 12D and 13D of the Yellow Group and 14D, 16D, 18B, 18C and 18D of the Yellow-Orange Group. When dried the shriveled kernels measure approximately 3 mm in thickness, 9 mm in width and 14 mm in length. The colors of the shriveled kernels are primarily a medium tan, 163A, 164B, 164C, 165B and 165C of the Greyed-Orange Group.

*Use*.—The subject variety, 'TRH3C113LW', is considered to be a low chill peach tree of early mid-season maturity, which produces subacid, white-fleshed fruit which are firm with a 60-80% red blush over a light yellow ground color, and which are useful for the fresh fruit market.

*Keeping quality*.—Average. Retains firmness and flavor after 14 days of refrigeration at 3-5° C.

*Resistance to insects and disease*.—No atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Pleasanton, Somerville and Fairfield, it will be understood that variations of the usual magnitude and characteristics incident to the changes in growing conditions, fertilization, pruning, and pest control are to be expected.

What is claimed is:

1. A new and distinct variety of peach tree named 'TRH3C113LW', as illustrated and described herein.

* * * * *